(12) United States Patent
Stewart et al.

(10) Patent No.: US 11,278,349 B2
(45) Date of Patent: Mar. 22, 2022

(54) INTRACARDIAC TOOLS AND METHODS FOR DELIVERY OF ELECTROPORATION THERAPIES

(71) Applicant: Medtronic Ablation Frontiers LLC, Minneapolis, MN (US)

(72) Inventors: Mark T. Stewart, Lino Lakes, MN (US); Jordon D. Honeck, Maple Grove, MN (US)

(73) Assignee: Medtronic Ablation Frontiers LLC, Minneapolis, MN (US)

( * ) Notice: Subject to any disclaimer, the term of this patent is extended or adjusted under 35 U.S.C. 154(b) by 1253 days.

(21) Appl. No.: 14/930,048

(22) Filed: Nov. 2, 2015

(65) Prior Publication Data
US 2016/0051324 A1 Feb. 25, 2016

Related U.S. Application Data

(63) Continuation of application No. 13/194,259, filed on Jul. 29, 2011, now abandoned.

(51) Int. Cl.
*A61B 18/14* (2006.01)
*A61N 1/32* (2006.01)
*A61B 18/00* (2006.01)

(52) U.S. Cl.
CPC .......... *A61B 18/1492* (2013.01); *A61N 1/327* (2013.01); *A61B 2018/00357* (2013.01); *A61B 2018/00613* (2013.01); *A61B 2018/1435* (2013.01)

(58) Field of Classification Search
CPC ..... A61B 18/12; A61B 18/1266; A61B 18/14; A61B 18/1442; A61B 18/1445; A61B 18/1448; A61B 18/1492; A61B 2018/00357; A61B 2018/00613; A61B 2018/1435; A61N 1/327
USPC .................................................... 606/33–50
See application file for complete search history.

(56) References Cited

U.S. PATENT DOCUMENTS

| 6,129,724 | A | 10/2000 | Fleischman et al. |
| 6,572,612 | B2 | 6/2003 | Stewart et al. |
| 2004/0082947 | A1 | 4/2004 | Oral et al. |
| 2005/0261672 | A1 | 11/2005 | Deem et al. |

(Continued)

FOREIGN PATENT DOCUMENTS

| CN | 101426551 A | 5/2009 |
| WO | 9510226 A1 | 4/1995 |

(Continued)

OTHER PUBLICATIONS

C.R. Bard, Inc., Ablation Redefined, Bard* HD Mesh Ablator Catheter, A Complete AF Procedural Solution, LT04Z0148/ Rev. 00/01-07, 2 pages.

(Continued)

*Primary Examiner* — Khadijeh A Vahdat
(74) *Attorney, Agent, or Firm* — Christopher & Weisberg, P.A.

(57) ABSTRACT

A medical system, including a medical device having a plurality of deployable arms, and at least one electrode on at least one of the plurality of arms; and an electric signal generator in communication with the medical device, the electric signal generator programmed to deliver pulsed energy to the medical device sufficient to induce irreversible electroporation ablation.

9 Claims, 9 Drawing Sheets

(56) References Cited

U.S. PATENT DOCUMENTS

| | | |
|---|---|---|
| 2005/0288730 A1 | 12/2005 | Deem et al. |
| 2006/0089637 A1 | 4/2006 | Werneth et al. |
| 2006/0293730 A1 | 12/2006 | Rubinsky et al. |
| 2007/0156135 A1 | 7/2007 | Rubinsky et al. |
| 2007/0203549 A1 | 8/2007 | Demarais et al. |
| 2008/0132885 A1 | 6/2008 | Rubinsky et al. |
| 2009/0248012 A1 | 10/2009 | Maor et al. |
| 2009/0281477 A1 | 11/2009 | Mikus et al. |
| 2010/0023004 A1 | 1/2010 | Francischelli et al. |
| 2010/0249771 A1 | 9/2010 | Pearson et al. |
| 2010/0250209 A1 | 9/2010 | Pearson et al. |
| 2010/0261994 A1 | 10/2010 | Davalos et al. |
| 2011/0238058 A1 | 9/2011 | van den Biggelaar et al. |
| 2012/0310237 A1* | 12/2012 | Swanson ................. A61B 18/08 606/41 |

FOREIGN PATENT DOCUMENTS

| | | |
|---|---|---|
| WO | 2007079438 A2 | 7/2007 |
| WO | 2009121017 A1 | 10/2009 |

OTHER PUBLICATIONS

China National Intellectual Property Administration, Notice on the First Office Action and Search Report for corresponding Application No. 201910110823.2, dated Dec. 10, 2020, 20 pages.

International Search Report and Written Opinion dated Mar. 12, 2012, for corresponding International Application No. PCT/US2012/046617; International Filing Date: Jul. 13, 2012 consisting of 13 pages.

European Patent Office, European Search Report dated Apr. 28, 2020 for corresponding Application No. EP 19218891, 9 pages.

* cited by examiner

INTRACARDIAC TOOLS AND METHODS FOR DELIVERY OF ELECTROPORATION THERAPIES

CROSS-REFERENCE TO RELATED APPLICATION

This application is a continuation of and claims priority to patent application Ser. No. 13/194,259, filed Jul. 29, 2011, entitled INTRACARDIAC TOOLS AND METHODS FOR DELIVERY OF ELECTROPORATION THERAPIES, now abandoned, the entirety of which is incorporated herein by reference.

STATEMENT REGARDING FEDERALLY SPONSORED RESEARCH OR DEVELOPMENT n/a

FIELD OF THE INVENTION

The present disclosure relates to medical systems and methods of use thereof for treating tissue, and more particularly, towards the treatment of cardiac tissue using high voltage energy delivery for irreversible electroporation (IEP) ablation.

BACKGROUND OF THE INVENTION

There are many medical treatments that involve instances of cutting, ablating, coagulating, destroying, or otherwise changing the physiological properties of tissue. These techniques can be used beneficially to change the electrophysiological properties of tissue, such as those associated with cardiac arrhythmias or other electrophysiological abnormalities. In particular, normal sinus rhythm of the heart begins with the sinoatrial node ("SA node") generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular node ("AV node") and the bundle of HIS to myocardial tissue cells of the ventricles. The depolarization of cells propagates across the ventricles, causing the ventricles to contract. This conduction system results in the described, organized sequence of myocardial contraction leading to a normal heartbeat.

Sometimes, anatomical obstacles in the atria or ventricles can lead to aberrant conductive pathways in heart tissue that disrupt the normal path of depolarization events. These anatomical obstacles or "conduction blocks" can cause the electrical impulse to degenerate into several circular wavelets that circulate about the obstacles. The aberrant conductive pathways create abnormal, irregular, and sometimes life-threatening heart rhythms called arrhythmias. An arrhythmia can take place in the atria, for example, as in atrial tachycardia, atrial fibrillation ("AF"), or atrial flutter. The arrhythmia can also take place in the ventricle, for example, as in ventricular tachycardia.

One approach to treating an arrhythmia includes creating one or more lesions that compartmentalize the aberrant pathway and direct electrical conduction along selected pathways to promote organized signal conduction, while also isolating AF triggers from connecting with the atria. A surgical approach called the "Maze" procedure (and variations of the Maze procedure) was designed to eliminate atrial fibrillation permanently. The procedure employs incisions in the right and left atria which divide the atria into electrically isolated portions that in turn results in an orderly passage of the depolarization wave front from the SA node to the AV node while preventing reentrant wave front propagation.

A less invasive approach includes selective ablation of offending regions of cardiac tissue. Conventionally, cardiac tissue ablation is effectuated by placement of one or more ablating members (e.g., electrodes, thermal-transfer elements, etc.), and applying energy at certain levels to destroy cells at the ablation site while leaving the surrounding structures of the organ largely intact. Radiofrequency ("RF") energy and cryogenic cooling have been found to be highly viable in this regard, and are commonly employed. Other ablative techniques include the application of ultrasound, microwave, laser, cytotoxic agents, etc.

However, these techniques are not without their potential drawbacks. A cryogenic ablation procedure typically requires extended cryogenic application time. A focal irrigated, radiofrequency ablation procedure typically requires approximately 35-45 minutes of actual energy delivery time. During that time, over a liter of saline may be infused into the patient to cool an RF electrode, which may present a problem of fluid overload in fluid compromised patients. Further, radiofrequency ablation may disrupt the cardiac endothelial surface, activate the extrinsic coagulation cascade, and lead to char and thrombus formation, which in turn may lead to systemic thromboembolism. In view of such drawbacks, medical systems and methods of use thereof having improvements in safety, treatment duration, and efficacy are desirable.

SUMMARY OF THE INVENTION

The present disclosure advantageously provides a medical system, including a medical device having a plurality of substantially planar windings, where at least a portion of the plurality of substantially planar windings is electrically conductive; and an electrical pulse generator coupled to the electrically conductive portion, the electrical pulse generator programmed to deliver pulsed, high voltage monophasic or biphasic energy to the electrically conductive portion to induce irreversible electroporation of a targeted tissue region. The medical device may include an intravascular catheter body coupled to the plurality of substantially planar windings; the electrically conductive portion may include at least one electrode; and/or the plurality of substantially planar windings may include a substantially-continuous electrically conductive surface. The pulsed, monophasic or biphasic energy may include a plurality of pulses each having a cycle time of not more than 5 milliseconds, but preferably not more than 50 microseconds; an output voltage between approximately 200-2000 volts, preferably between 500 and 1000 volts at a pulse width between approximately 0.005 microseconds-5 milliseconds, preferably between 0.005 microseconds and 50 microseconds; and/or a series of pulse trains, with each train having between approximately 1-500 monophasic or biphasic pulses, preferably 10-100 pulses. Delivery of energy pulse trains are preferably timed to correspond with the onset of depolarization of the myocardium. Alternately the pulse trains may be delivered to myocardium that is fully polarized, just before normal sinus rhythm activation occurs.

A medical system is provided, including a medical device having a plurality of deployable arms, and at least one electrode on at least one of the plurality of arms; and an electric signal generator in communication with the medical device, the electric signal generator programmed to deliver pulsed and/or biphasic energy to the medical device sufficient to induce irreversible electroporation ablation, including a plurality of pulses each having a cycle time of not more than 5 milliseconds, but preferably not more than 50 microseconds; an output voltage between approximately 200-2000 volts, preferably between 500 and 1000 volts at a pulse width between approximately 0.005 microseconds-5 milliseconds, preferably between 0.005 microseconds and 50 microseconds; and/or a series of pulse trains, with each train having between approximately 1-500 monophasic or biphasic pulses, preferably 10-100 pulses. The medical device may include a flexible catheter body; the plurality of deployable arms may be deployable into a substantially linear configuration; and/or the substantially linear configuration may be substantially transverse to a longitudinal axis of the catheter body. The medical device may include a selectively extendable needle electrode; the electrode may include an electrically conductive surface and an electrically insulated surface; and/or the electrode may include at least two electrically conductive surfaces separated by an electrically insulated surface.

A method of ablating cardiac tissue is provided, including positioning a first electrically conductive surface adjacent an endocardial surface of a heart; positioning a second electrically conductive surface adjacent an epicardial surface of the heart; and conducting pulsed energy between the first and second electrically conductive surfaces to induce irreversible electroporation ablation of tissue therebetween. At least one of the first and second electrically conductive surfaces may include a plurality of electrically conductive coils and/or at least one of the first and second electrically conductive surfaces may include a plurality of electrodes disposed on a plurality of deployable arms of a catheter. The pulsed energy may include a plurality of monophasic or biphasic pulses, with pulse durations, cycle times, and amplitudes as described previously. The individual electrodes may be held out of phase with one another such that bipolar energy is driven between the selected out of phase electrodes. This may include alternating out of phase electrodes on the deployable endocardial contact arms or in combination with the electrode or electrodes on the deployable needle. The deployable needle provides the ability to deliver energy deeper into the tissues, which may be required in the case of ventricular myocardial ablations. The method of delivering energy may include obtaining and/or monitoring an electrocardiogram of the heart, and where conducting the pulsed energy includes timing conduction of the energy with at least one selected segment of the electrocardiogram. The selected segment may be indicative of the tissue to be ablated experiencing depolarization; may be a QRS wave segment; and/or may be a P wave segment.

A method of ablating cardiac tissue is provided, including positioning a first electrically conductive surface of a first medical device adjacent an endocardial surface of a heart; positioning a second electrically conductive surface of a second medical device spaced away from the first electrically conductive surface; and conducting pulsed energy between the first and second electrically conductive surfaces to induce irreversible electroporation ablation of tissue therebetween. At least one of the first and second electrically conductive surfaces may include a plurality of electrodes disposed on a plurality of deployable arms; at least one of the first and second medical devices may include a guide wire; and/or at least one of the first and second medical devices may include an inflatable element. The method may include substantially occluding an orifice with the first medical device. The second medical device may be positioned within a pulmonary vein; a coronary sinus; and/or a superior vena cava. The first medical device may be positioned adjacent a septal wall, and the second medical device may be positioned in a right atrium. The method may include conducting pulsed energy between a plurality of electrically conductive surfaces on the first medical device to induce irreversible electroporation ablation of tissue therebetween.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
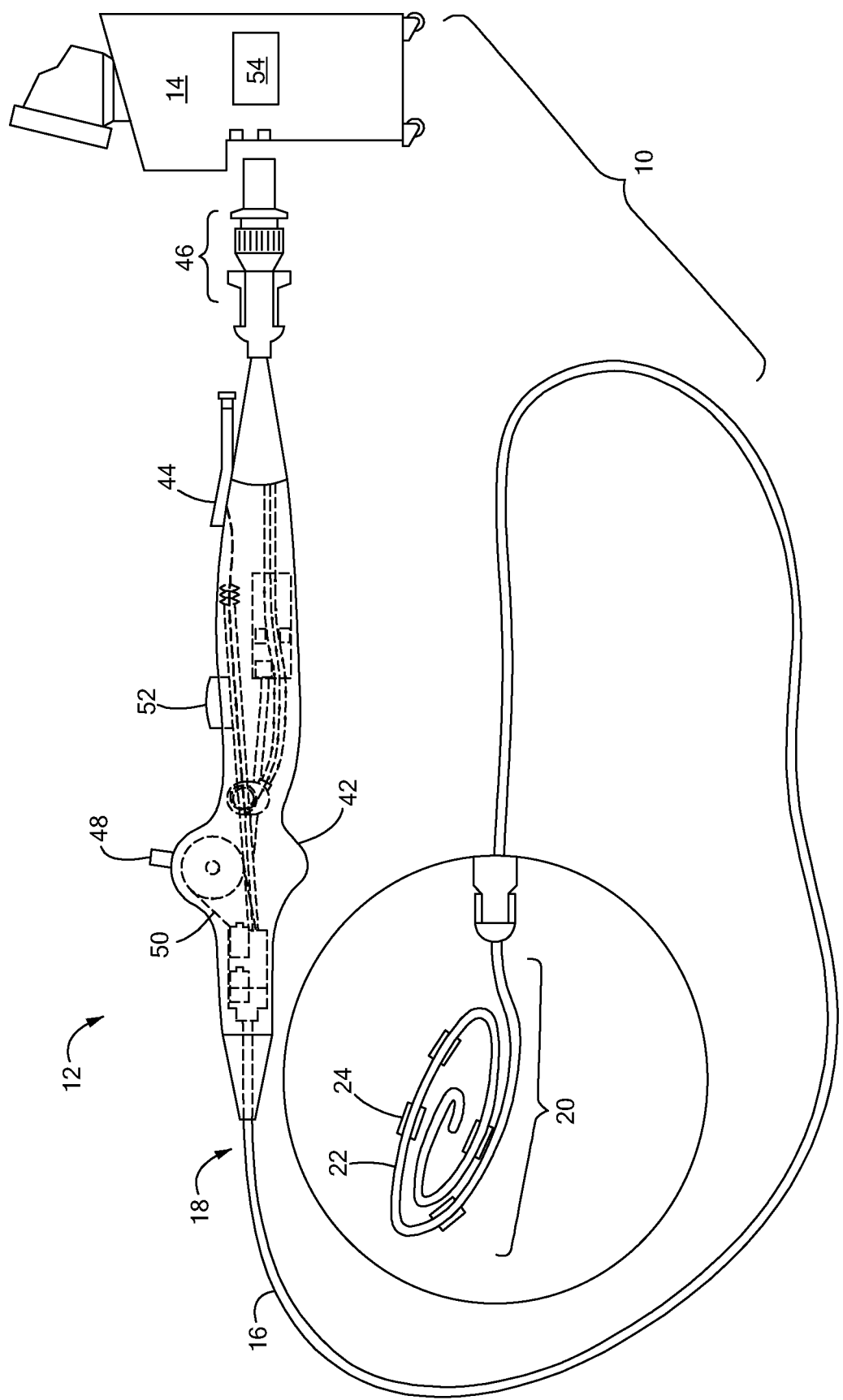
FIG. 1 is an illustration of an example of a medical system constructed in accordance with the principles of the present invention.

The present invention advantageously provides methods and systems for diagnosing and/or treating undesirable physiological or anatomical tissue regions, such as those contributing to aberrant electrical pathways in the heart. Referring now to the drawing figures in which like reference designations refer to like elements, an embodiment of a medical system constructed in accordance with principles of the present invention is shown in FIG. 1 and generally designated as "10." The system 10 generally includes a medical device 12 that may be coupled to a control unit 14 or operating console. The medical device 12 may generally include one or more diagnostic or treatment regions for energetic, therapeutic and/or investigatory interaction between the medical device 12 and a treatment site. The treatment region(s) may deliver, for example, electroporation energy to a tissue area in proximity to the treatment region(s).

Now referring to FIG. 1, the medical device 12 may include an elongate body 16 passable through a patient's vasculature and/or positionable proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion of the elongate body 16 and the distal portion of the elongate body 16.

The distal portion 20 may generally define the one or more treatment region(s) of the medical device that are operable to monitor, diagnose, and/or treat a portion of a patient. The treatment region(s) may have a variety of configurations to facilitate such operation. For example, as shown in FIG. 1, the distal portion may include a segment configurable or deployable into a plurality of windings 22. The windings 22 may include a segment traversing greater than a 360 degree circumference with a changing radius between one or more portions of the windings 22. Moreover, the windings 22 may be substantially planar with respect to one another, e.g., the windings 22 may have a decreasing radius such that one portion of the windings 22 circumscribes or surrounds another portion of the windings 22, with the windings 22 being oriented parallel to one another in a substantially single plane. The planar orientation of the windings 22 may facilitate ease of placement of the distal portion 20 of the device 12 into small, compact anatomical positions while achieving a large treatment or diagnoses surface area of the device. Accordingly, one or more portions of the windings 22 may include one or more electrically conductive surface(s) 24, such as one or more electrodes, or alternatively the windings 22 may constitute a substantially continuous electrically conductive surface along a substantial portion of their length.

Figure 2:
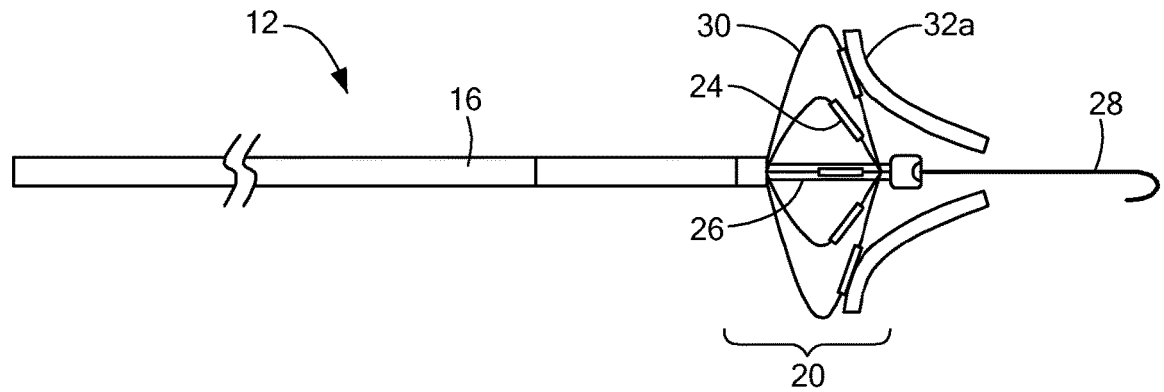
FIG. 2 is an illustration of an exemplary medical device for use with the system of FIG. 1.
Figure 3:
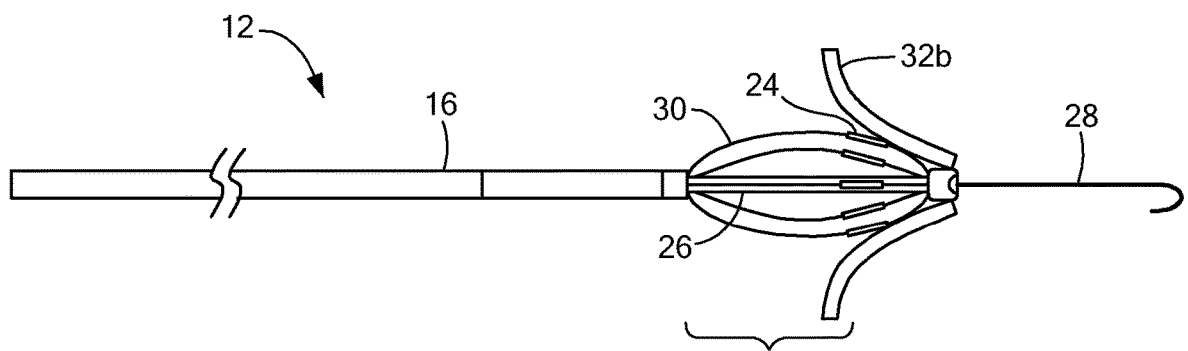
FIG. 3 is another illustration of the medical device of FIG. 2.

Turning to FIGS. 2-3, the distal portion 20 may include a shaft 26 at least partially disposed within a portion of the elongate body 16. The shaft 26 may extend or otherwise protrude from a distal end of the elongate body 16, and may be movable with respect to the elongate body 16 in longitudinal and rotational directions. That is, the shaft 26 may be slidably and/or rotatably moveable with respect to the elongate body 16. The shaft 26 may further define a lumen 24 therein for the introduction and passage of a guide wire 28 and/or another treatment or diagnostic instrument (not shown). The distal portion 20 may include one or more deployable arms 30 movably coupled to the shaft 26 and/or the elongate body 16, where one or more of the arms 30 may include an electrically conductive surface and/or electrode(s) 24 to deliver or conduct electrical pulses to a designated treatment area. The arms 30 may be disposed around a circumference of the shaft 26 and/or the elongate body 16, where the shaft 26 may be controllably moved to manipulate and expansions or radial distance between the arms 30 and the shaft/elongate body. The selectively adjustable radius of the arms 30 allows engagement and subsequent diagnosis or treatment of varying anatomical tissue structures which may include different geometries or dimensions. For example, as shown in FIG. 2, the arms 30 may be expanded to contact a larger radius or portion of a tissue wall or structure 32a. Turning to FIG. 3, the arms 30 may be manipulated into a smaller radius with respect to the shaft 26 and/or elongate body 16 to engage a vessel or lumen tissue structure 32b having a smaller diameter.

Figure 4:
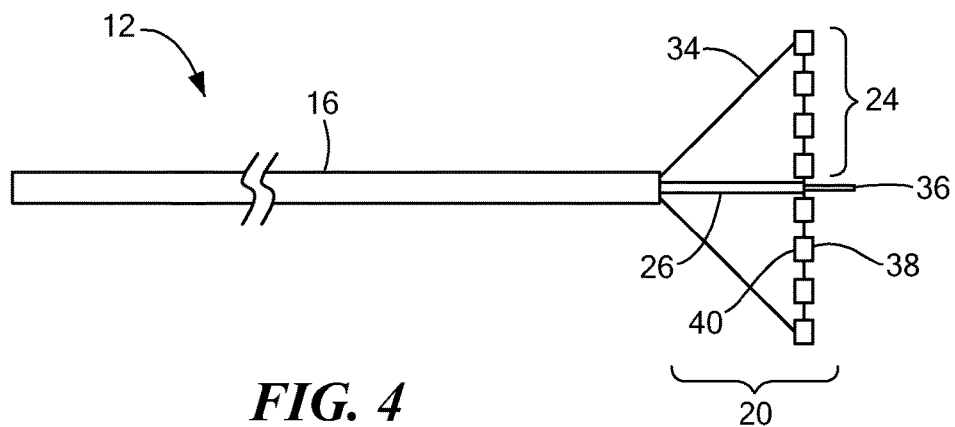
FIG. 4 is an illustration of another exemplary medical device for use with the system of FIG. 1.
Figure 5:
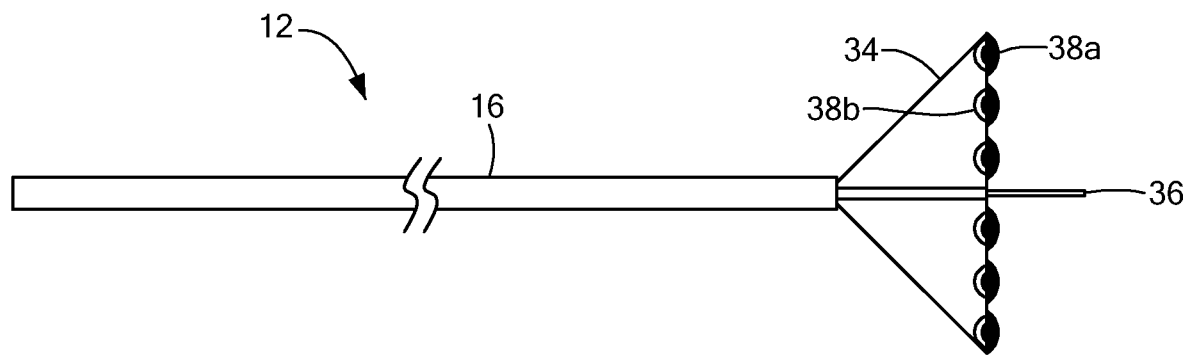
FIG. 5 is still another illustration of an exemplary medical device for use with the system of FIG. 1.

Referring now to FIGS. 4-5, the arms 30 may be extendable into a substantially linear configuration. For example, the arms 30 may attach to the shaft 26 through a hinge or other pivoting mechanism allowing the arms 30 to open substantially parallel to one another and substantially transverse to the shaft or a longitudinal axis of the elongate body. The extension and/or retraction of the arms 30 may be facilitated in part by one or more steering wires 34 coupled to portions of the arms 30, and/or one or more expandable elements positioned within or otherwise coupled to the arms 30, as described in more detail below. The medical device 12 may also include a needle 36 that is controllably extendable and retractable from a distal portion of the device 12, such as the shaft 26 or elongate body 16. The needle 36 may include an electrically conductive surface to aid in mapping, ablating or otherwise electrically interacting with a targeted tissue region, such as that in the heart for example. Further, the needle 36 may aid in anchoring or securing the distal portion of the device 12 to the desired anatomy. The conductive surface or surfaces of the needle may include raised profile or larger diameter conductive features or rings to effect improved local depolarization of myocardial cells to allow measurement of the repolarization of cells surrounding those depolarized cells. The needle 36 may also be employed to deliver agents, including electrolytes such as sodium, potassium, or calcium to alter the ionic balance of cells exposed to electroporative energy deliveries, thereby enhancing the lethality of such energy deliveries to such tissues exposed to the delivered agents and energy applications.

The electrically conductive regions and/or electrodes 24 described above may include variations in their electrically conductive and isolative characteristics. For example, as shown in FIG. 4, the electrodes 24 may include a highly conductive first surface or face 38 oriented in the direction where contact or engagement with a tissue site is likely to occur, i.e., such as a distal face or surface. The electrodes 24 may further include less conductive, insulated segment or portion 40 on the regions of the electrode or surface less likely to contact or interact with tissue to be diagnosed or treated, such as a proximally-facing or oriented surface or portion of the electrode. The insulated portion 40 can increase the efficiency of the device 12 by directing diagnostic or treatment energies towards the engaged parts of the device 12. Further, the electrodes 24 may be divided into two or more electrically conductive portions delineated or separated by an electrically insulated segment. For example, as shown in FIG. 5, the electrodes 24 may include a distally-facing surface 38a to engage tissue for treatment, while a proximally-facing surface includes a second conductive surface 38b providing an electrical reference point that is electrically isolated from the distally-facing surface 38a. The distally (tissue)-facing conductive surface 38a may include geometrical characteristics or dimensions to evoke a monophasic action potential when in contact with a designated tissue site. Such geometrical characteristics would include raised features that result in a higher local myocardial tissue contact pressure, directly under such features. Such pressure causes local sustained depolarization of the underlying myocardial tissue, thereby allowing the measurement of a monophasic action potential signal from the myocardial tissue site when referenced against a proximal, non-myocardial tissue-facing or non myocardial tissue-contacting electrode.

Referring again to FIG. 1, the medical device 12 may include a handle 42 coupled to the proximal portion of the elongate body 16. The handle 42 can include circuitry for identification and/or use in controlling of the medical device 12 or another component of the system 10. Additionally, the handle 42 may be provided with a fitting 44 for receiving a guide wire or another diagnostic/treatment instrument that may be passed into the lumen of the shaft. The handle 42 may also include connectors 46 that are matable to the control unit 14 to establish communication between the medical device 12 and one or more components or portions of the control unit 14.

The handle 42 may also include one or more actuation or control features that allow a user to actively control, deflect, steer, or otherwise manipulate a distal portion of the medical device 12 from the proximal portion of the medical device 12. For example, the handle 42 may include one or more components such as a lever or knob 48 for manipulating the elongate body 16 and/or additional components of the medical device 12. For example, a pull wire 50 with a proximal end and a distal end may have its distal end anchored to the elongate body 16 at or near the distal portion 20. The proximal end of the pull wire 50 may be anchored to an element such as a cam in communication with and responsive to the lever 48. The medical device 12 may include an actuator element 52 that is movably coupled to the proximal portion of the elongate body 16 and/or the handle for the manipulation and movement of a portion of the medical device 12, such as the shaft 26 or the arms 30, for example. The actuator element 52 may include a thumb-slide, a push-button, a rotating lever, or other mechanical structure for providing a movable coupling to the elongate body 16, the handle 42, and/or the shaft 26. Moreover, the actuator element 52 may be movably coupled to the handle 42 such that the actuator element 52 is movable into individual, distinct positions, and is able to be releasably secured in any one of the distinct positions. In addition, the arms 24 shown in FIG. 4 may be passively deployed upon exit from a delivery sheath (not shown). For example, the struts 34 may be constructed of a superelastic material such as a nickel-titanium alloy. In such a configuration, mechanical control wires would not be required to deploy the arms 30. Retraction of the device into a delivery sheath would cause the arms 30 to compress and allow the device 12 to exit the body. Additionally, the shaft 26 may be employed to apply retraction or extension force to the junction point of the arms 30 to aid in retraction or enhance contact with complex tissue morphologies. The shaft 26 may also provide a conduit or lumen for controllable deployment of the needle 36.

The system 10 may include one or more treatment or diagnostic sources coupled to the medical device 12 for use in an operative procedure, such as irreversible electroporation ablation, for example. For example, the control unit 14 may include a treatment energy source 54 as a treatment or diagnostic mechanism in communication with one or more portions of the medical device 12. The treatment energy source 54 may include an electrical current or pulse generator having a plurality of output channels, with each channel coupled to an individual electrode or electrically conductive portion 24 of the medical device 12. The treatment energy source 54 may be operable in one or more modes of operation, including for example: (i) bipolar energy delivery between at least two electrodes 24 or electrically-conductive portions (such as the needle 36, for example) of the medical device 12 within a patient's body, (ii) monopolar or unipolar energy delivery to one or more of the electrodes or electrically-conductive portions on the medical device 12 within a patient's body and through a patient return or ground electrode spaced apart from the electrodes of the medical device 12, such as on a patient's skin or on an auxiliary device positioned within the patient away from the medical device 12, for example, and (iii) a combination of the monopolar and bipolar modes.

The treatment energy source 54 may provide electrical pulses to the medical device 12 to perform an electroporation procedure. "Electroporation" utilizes high electric field amplitude electrical pulses to effectuate a physiological modification (i.e., permeabilization) of the cells to which the energy is applied. Such pulses may preferably be short (e.g., nanosecond, microsecond, or millisecond pulse width) in order to allow application of high voltage without large flow of electrical current that would result in significant tissue heating. In particular, the pulsed energy induces the formation of microscopic pores or openings in the cell membrane. Depending upon the characteristics of the electrical pulses, an electroporated cell can survive electroporation (i.e., "reversible electroporation") or die (i.e., irreversible electroporation, "IEP"). Reversible electroporation may be used to transfer agents, including large molecules, into targeted cells for various purposes.

The treatment energy source 54 may be configured and programmed to deliver pulsed, high voltage electric fields as described below, appropriate for achieving desired pulsed, high voltage ablation (or IEP ablation). As a point of reference, the pulsed, high voltage ablation effects of the present disclosure are distinguishable from DC current ablation, as well as thermally-induced ablation attendant with conventional RF techniques. The IEP in accordance with the present disclosure is sufficient to induce cell death for purposes of completely blocking an aberrant conductive pathway along or through cardiac tissue, destroying the ability of the so-ablated cardiac tissue to propagate or conduct cardiac depolarization waveforms and associated electrical signals.

To that end, the treatment energy source 54 may deliver a number of different various waveforms or shapes of pulses to achieve electroporation ablation of cardiac tissue, including sinusoidal AC pulses, DC pulses, square wave pulses, exponentially decaying waveforms, or other pulse shapes such as combined AC/DC pulses, or DC shifted signals. The parameters of pulsed energy generated by the treatment energy source 58 can vary in one or more of the following manners: waveform shape, pulse polarity, amplitude, pulse duration, interval between pulses, number of pulses (frequency), combination of waveforms, etc. One or more of these parameters can be altered or changed during the ablation procedure. For example, the treatment energy source 58 may be adapted to generate a high density energy gradient in the range of 10-1,000 V/cm, pulsed at rates on the order of 0.001-1,000 microseconds. The voltage level, pulse rate, waveform, and other parameters can be varied as described below, with the control unit 14 including, in some embodiments, a controller that automatically dictates operational parameters as a function of one or more characteristics of the cardiac tissue target site (e.g., tissue type (such as fatty tissue, thickness, cell orientation, naturally-occurring electrical activity, etc.)).

The treatment energy source 54 may be configured to deliver monophasic or biphasic electrical pulses to one or more electrically conductive portions of the medical device. As a point of reference, while monophasic electrical pulses may alternatively be employed, the application of biphasic electrical pulses has surprisingly been found to produce unexpectedly beneficial results in the context of cardiac tissue ablation. With biphasic electroporation pulses, the direction of the pulses completing one cycle alternates in less than a few hundred microseconds. As a result, the cells to which the biphasic electrical pulses are applied undergo alternation of electrical field bias. With IEP cardiac tissue ablation, changing the direction of bias surprisingly helps to reduce prolonged post-ablation depolarization and/or ion charging. As a result, it reduces prolonged muscle excitation (e.g., skeletal and cardiac cells) and risks of post shock fibrillation of the cardiac cells. Further, biphasic electrical pulses overcome the high impedance characteristics of fatty cells often times associated with cardiac ablation procedures. Thus, biphasic electrical pulses avoid the possible drawbacks of monophasic electrical pulses including: 1) atrial or ventricular fibrillation, 2) less effective in making lesions through fat, 3) propensity to make thermal lesions on the anode side of an electrode pair, and 4) prolonged muscle excitation.

> With respect to biphasic energy, the treatment energy source may be programmed to deliver a series of pulse trains that are timed to be delivered at the onset of local depolarization, each train preferably not lasting more than about 50 milliseconds to avoid energy delivery outside of the absolute refractory period. Each train can consist of 10 to 60 biphasic (i.e., half positive phase and half negative phase) pulses. With these applications, an output voltage from the treatment energy source can be in the range of 200-1000 volts at currents in the range of 8-25 Amps. These output voltage levels (200-1000 volts) provide a voltage intensity delivered by the medical device 12 on the order of 200-1000 V/cm across 10 mm thick tissue, for example.

The control unit 14 and/or the treatment energy source 54 may include one or more controllers, processors, and/or software modules containing instructions or algorithms to provide for the automated operation and performance of the features, sequences, calculations, or procedures described herein. The system 10 may further include one or more sensors to monitor the operating parameters throughout the system 10, including for example temperature, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. Such sensors may be employed to evaluate electrical path impedance prior to delivery of high voltage energy by delivering on or more low voltage test pulses to evaluate the tissue electrical path.

In an exemplary use of the medical system 10, the distal portion 20 of the medical device 12 may be positioned in proximity to a tissue region to be treated. In particular, the distal portion 20 may be positioned to contact an endocardial tissue region, such as a substantially continuous portion of an atrial wall, a circumference of a blood vessel such as a pulmonary vein, or the like. The distal portion 20 may be manipulated into the desired geometric configuration, including a selected radius of the windings 22, selective expansion or deployment of the arms 30, or the like through the actuator element 52 or other control or steering mechanism(s) operable at the handle 42.

The electrically-conductive portions 24 of the distal portion 20 may be used to measure and/or record electrical signals or conduction pathways in the contacted tissue region, commonly referred to as "mapping." The targeted tissue region may be mapped to identify the location of abnormal signal pathways for subsequent therapy or treatment. Once attaining the desired device position, configuration and/or confirmation that a tissue site is problematic, the medical device 12 may be used to treat the designated tissue area.

Figure 6:
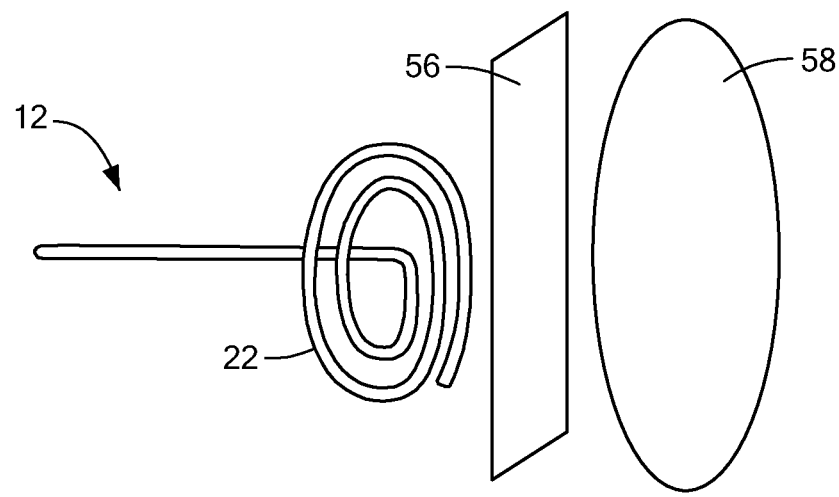
FIG. 6 is an illustration of an exemplary use of a medical in accordance with the principles of the present invention.
Figure 7:
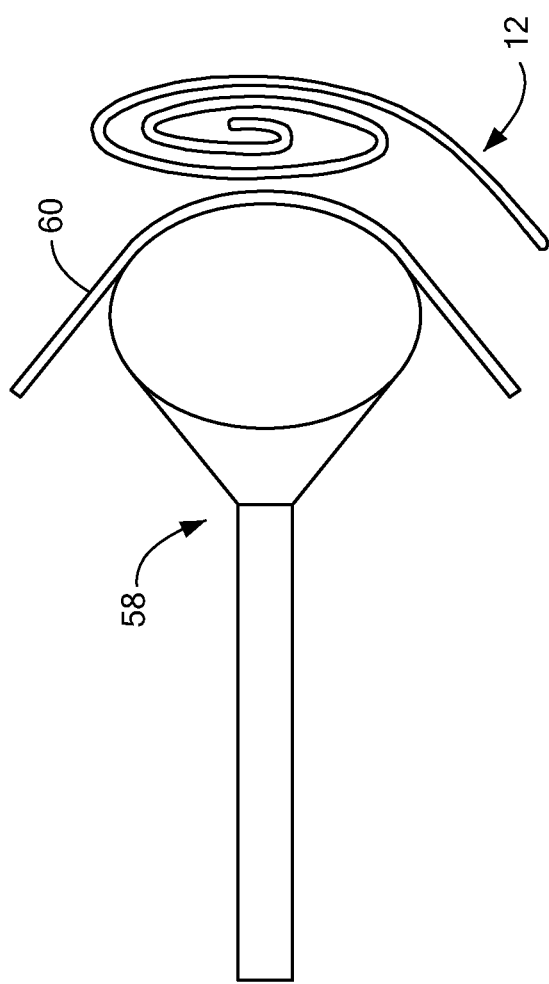
FIG. 7 is another illustration of an exemplary use of a medical in accordance with the principles of the present invention.

For example, the medical device 12 may be operated to deliver electroporating energy pulses through the conductive portions 24 of the distal portion 20 to achieve IEP ablation of the targeted tissue. Referring to FIG. 6, for example, the medical device 12 having the plurality of windings 22 may be positioned adjacent an endocardial surface 56 of the heart, while a return electrode or other secondary electrically conductive tool 58 may be positioned away from the medical device, such as on an epicardial surface 60 of the heart or affixed on an exterior surface of the patient, to complete the circuit for electrical delivery. Alternatively, the medical device 12 may be placed adjacent to an epicardial surface 60 of the heart, such as within the pericardial space, with another medical device or instrument 58 (which may include, for example, a second medical device similar to any of the configurations of the medical device 12 described herein or in application Ser. No. 13/194,180, filed Jul. 29, 2011, entitled "Mesh-Overlayed Ablation and Mapping Device," the entirety of which is hereby incorporated by reference) residing on an interior or endocardial position of the heart for electrical conduction between the two devices, and thus the tissue disposed therebetween (as shown in FIG. 7). As mentioned above, the substantially planar windings 22 provide a reduced profile easing insertion into compact spaces, such as within the pericardial space or near the atrial-ventricular groove region of the heart, to provide a local vector for energy flow between the windings and/or electrodes thereon and the electrodes on the intracardiac device.

Figure 8:
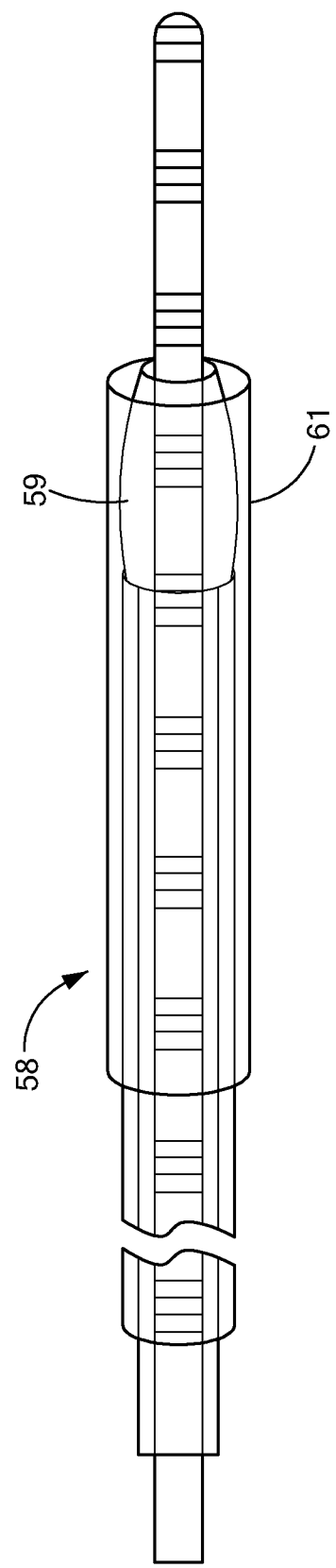
FIG. 8 is still another illustration of an exemplary medical device for use with the system of FIG. 1.

Aside from conducting IEP energy through an epicardial-endocardial device placement, a number of additional or alternative energy delivery vectors may also be implemented to create the desired ablative treatment patterns on the targeted tissue. For example, the medical device 12 may be positioned on the left atrial wall, with electrodes contacting the endocardium in proximity to the ostium of the left inferior pulmonary vein, extending to the annulus of the mitral valve. The secondary electrically conductive tool 58 may be placed within the coronary sinus or in the pericardial space, adjacent the medical device 12. Now referring to FIG. 8, an exemplary configuration of the secondary electrically conductive tool 58 may include a diagnostic catheter or intravenous device, such as a coronary sinus mapping catheter, with an expandable conductive mesh 59 coupled to and/or slidable along a body of the tool 58. The expandable mesh 59 serves as an energy return path from the medical device 12. In addition, the secondary electrically conductive tool 58 may include one or more slidable sheath(s) 61 slidably advanced over the body of the device 58 that can be advanced to a distal end of the tool 58 to selectively cover or expose conductive portions of the mesh 59. The tool 58, including the sheath 61 and/or expandable mesh 59, may include one or more controllable mechanisms (not shown) such as pull-wires or the like to selectively control the exposure and/or expansion of the mesh. The mesh 59 may be biased towards a particular expanded configuration or shape, where the one or more sheaths 61 are manipulated to restrict or allow the biased configuration of the mesh 59.

Figure 9:
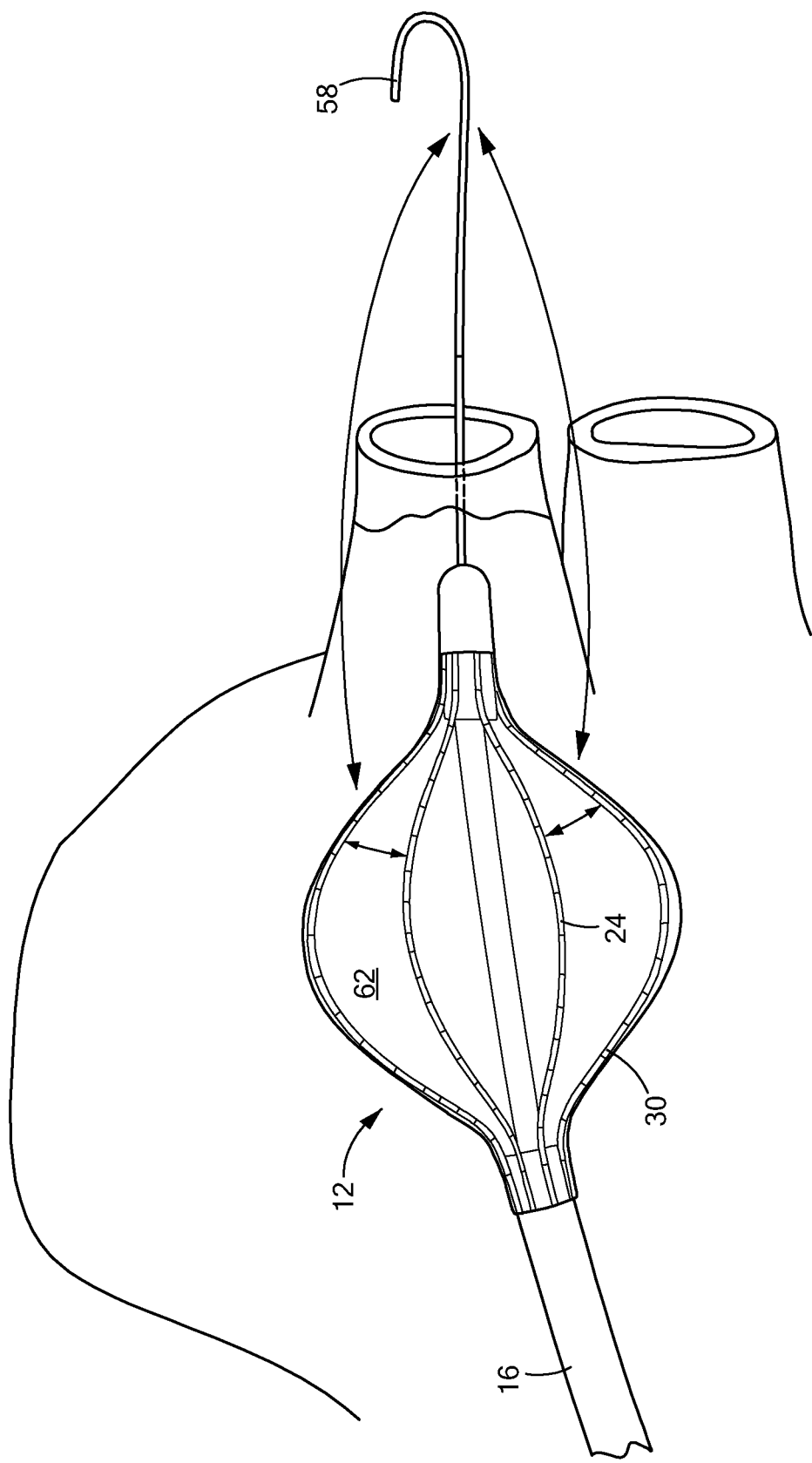
FIG. 9 is yet another illustration of an exemplary use of a medical in accordance with the principles of the present invention.

Another example, as shown in FIG. 9, the medical device 12 is shown positioned in an endocardial space, such as an atrium of the heart. The medical device 12 may include an expandable or inflatable element 62 operable to expand or otherwise control the position or configuration of the arms 30 and the electrodes 24. The inflatable element 62 may be positioned such that it occludes an orifice in the heart wall, such as an ostium of a pulmonary vein. In addition, the secondary electrically conductive tool 58 may include a guide wire passable through the medical device 12 such that a portion of the guide wire extends distally from the medical device 12 into the pulmonary vein. The distally-extending portion of the guide wire may include one or more electrically conductive surfaces 64 for the conduction of one or more electrical pulses (1) between the electrically conductive surface(s) 64 and the electrodes 24 of the medical device 12, and/or (2) between two or more of the electrodes on the medical device 12, as indicated by the illustrated arrows. This energy delivery vector may provide both longitudinal and circumferential treatment patterns in the affected tissue.

Figure 10:
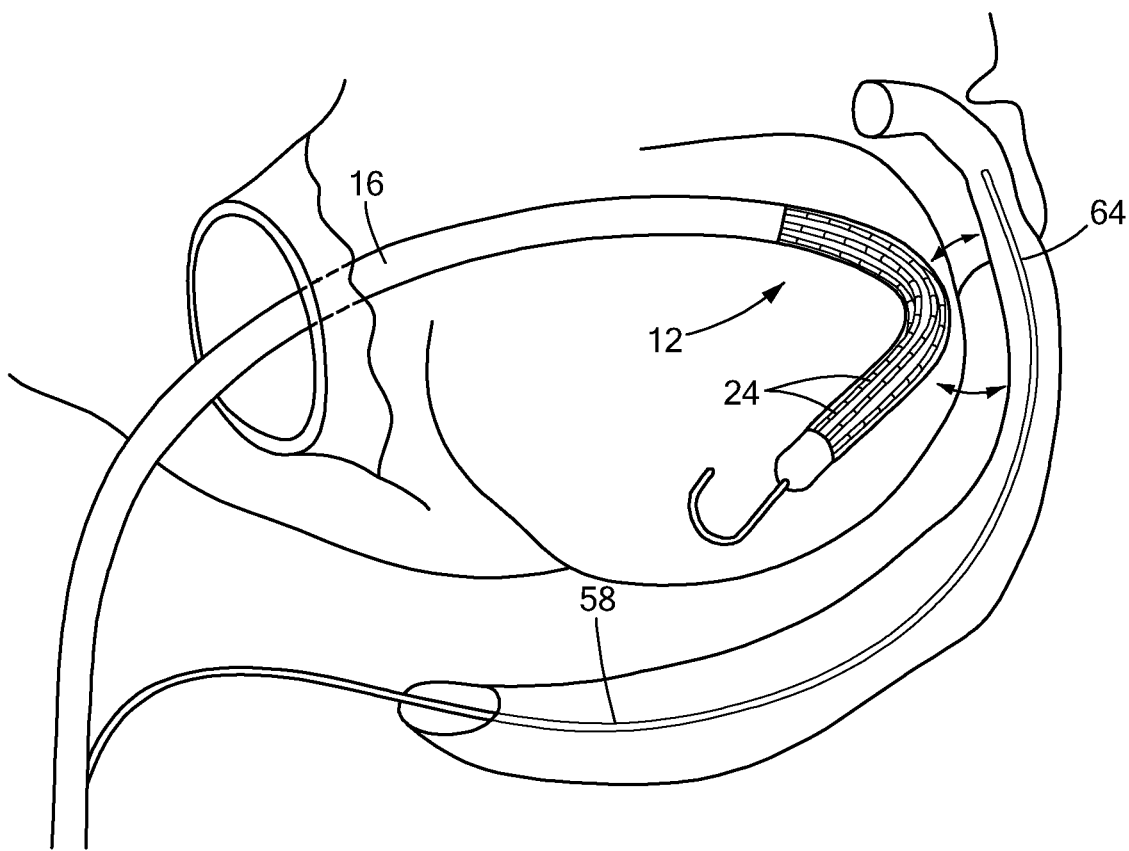
FIG. 10 is still another illustration of an exemplary use of a medical in accordance with the principles of the present invention.
Figure 11:
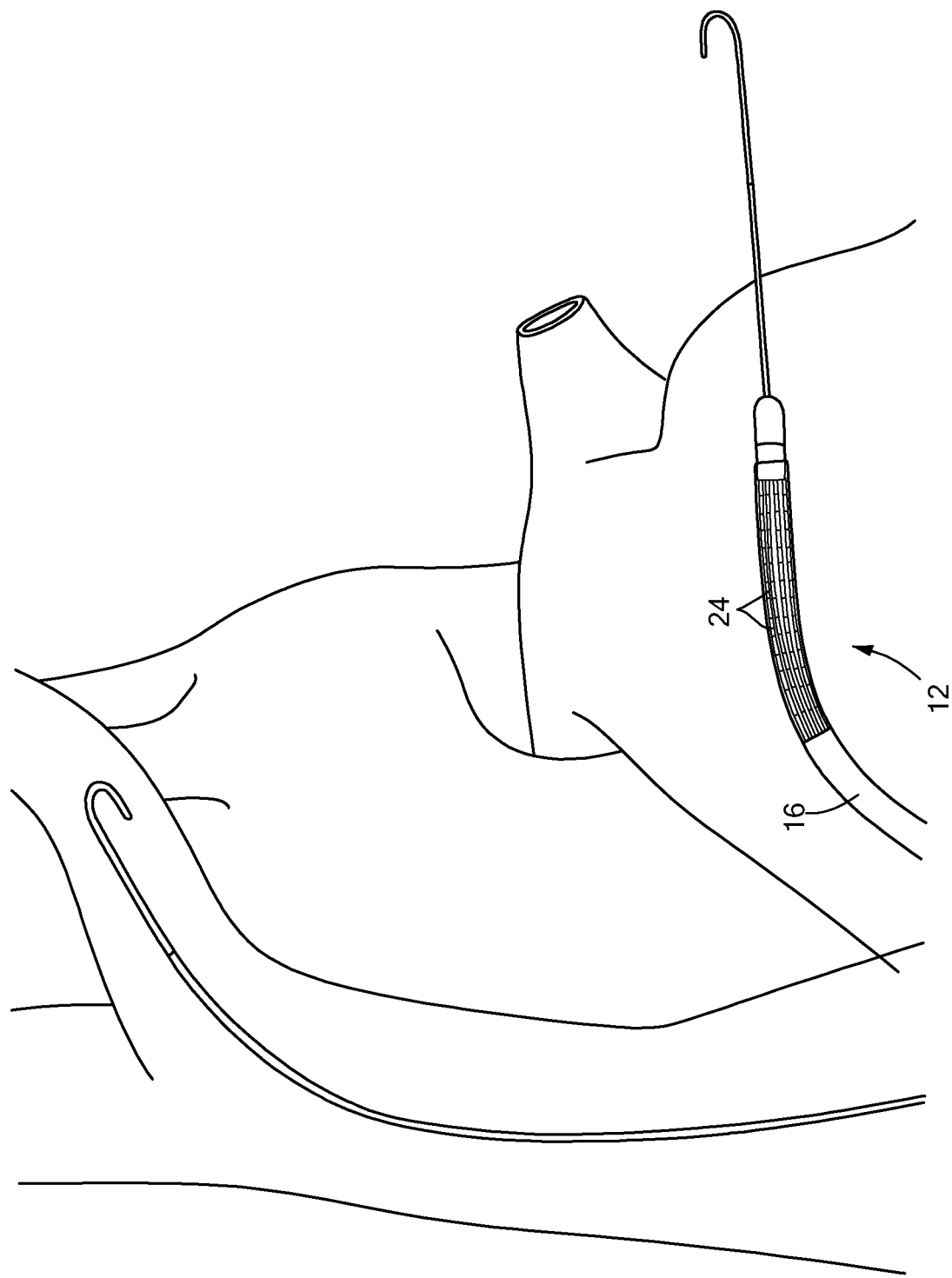
FIG. 11 is another illustration of an exemplary use of a medical in accordance with the principles of the present invention.

Turning now to FIG. 10, the medical device 12 may be positioned along an endocardial wall or surface while the secondary electrically conductive tool 58, which may include a guide wire, is routed through a portion of the coronary sinus. One or more electrical pulses may be conducted between the electrodes 24 of the medical device 12 and the electrically conductive surface(s) 64 of the secondary electrically conductive tool 58, as indicated by the illustrated arrows. This energy delivery vector may provide substantially linear or curvilinear treatment patterns in the affected tissue when treating the mitral isthmus region, for example. As shown in FIG. 11, the medical device 12 may be positioned against an upper wall or roof of an atrium, while the secondary electrically conductive tool 58 is routed through a portion of the superior vena cava and/or left subclavian vein. One or more electrical pulses may be conducted between the electrodes 24 of the medical device 12 and the electrically conductive surface(s) 64 of the secondary electrically conductive tool 58, as indicated by the illustrated arrows. This energy delivery vector may also provide substantially linear or curvilinear treatment patterns in the affected tissue.

Figure 12:
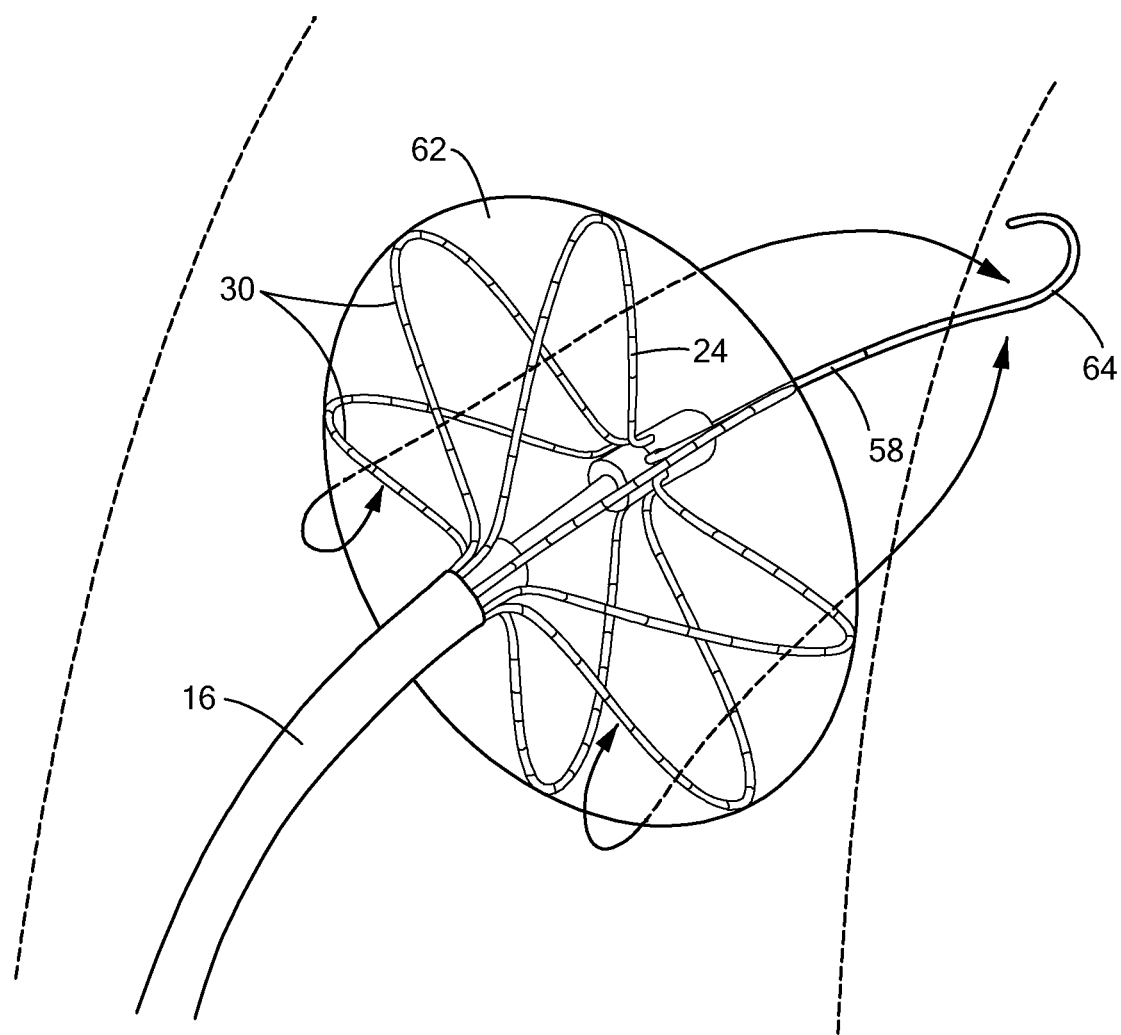
FIG. 12 is yet another illustration of an exemplary use of a medical in accordance with the principles of the present invention.
Figure 13:
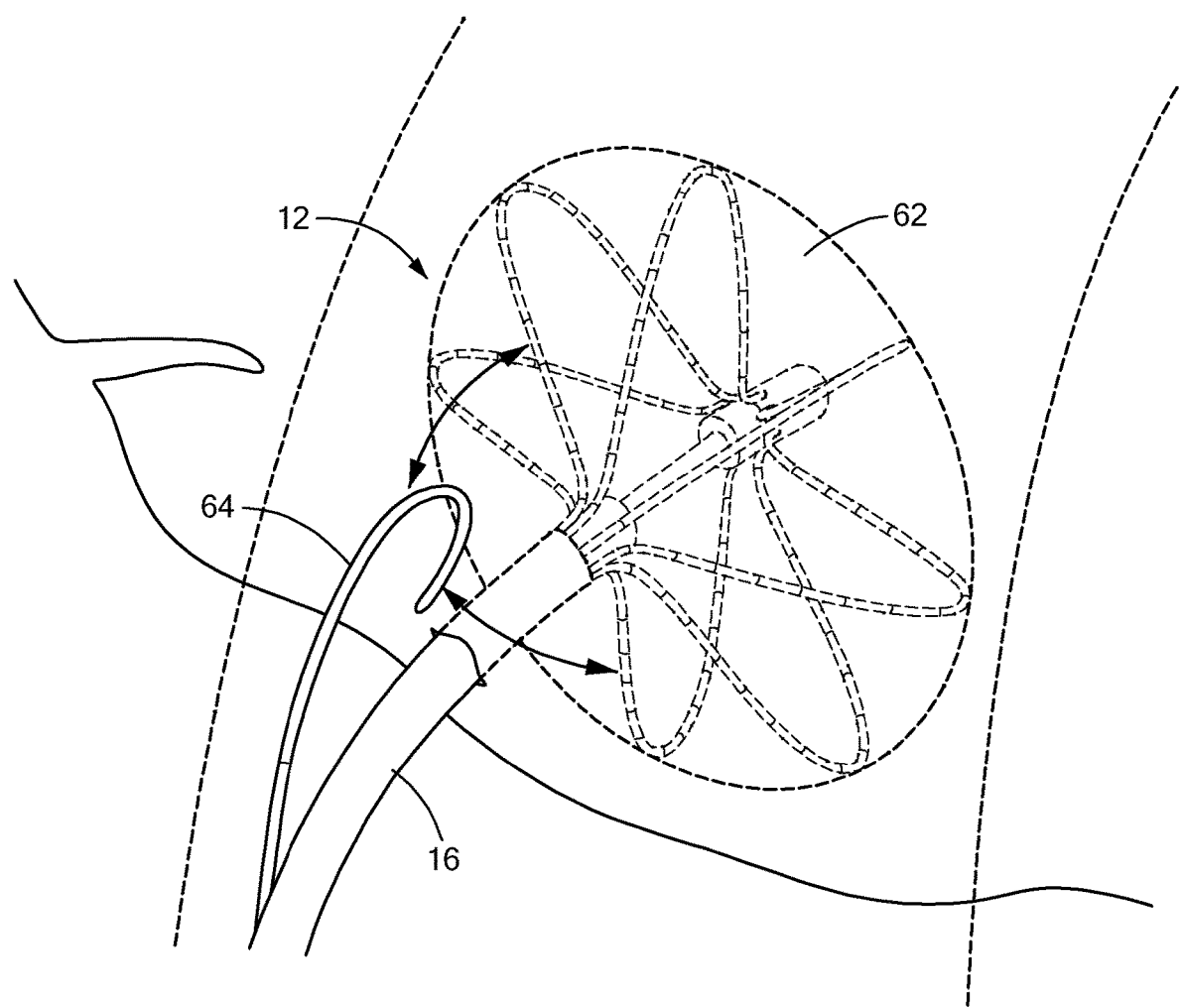
FIG. 13 is still another illustration of an exemplary use of a medical in accordance with the principles of the present invention.

Turning now to FIG. 12, the medical device 12 may be positioned with a proximal portion of the arms 30 and/or electrodes 24 against a septal wall. The secondary electrically conductive tool 58 may be passed through the medical device 12 such that a portion of the guide wire extends distally from the medical device 12 into the cardiac cavity. Alternatively, as shown in FIG. 13, the secondary electrically conductive tool 58 may be positioned proximally of the electrodes 24 and/or on an opposite side of the septal wall. One or more electrical pulses may be conducted (1) between the electrically conductive surface(s) 64 and the electrodes 24 of the medical device 12, and/or (2) between two or more of the electrodes on the medical device 12, as indicated by the illustrated arrows. This energy delivery vector may selectively provide longitudinal and/or circumferential treatment patterns in the affected tissue.

Varying the position and/or alignment of the one or more instituted medical devices may include epicardial placement into the pericardial space with alignment for vectored energy return from the medical device 12, with the secondary electrically conductive tool 58 deployed in alignment with the atrial-ventricular groove, adjacent the posterior left atrial wall near the left inferior pulmonary vein and mitral valve annulus. Such placement, for example, would promote energy vectoring to produce an effective "left atrial isthmus" lesion, connecting the left inferior pulmonary vein ostial region with the mitral valve annulus. In another example, the secondary electrically conductive tool 58 may be placed into the pericardial space and advanced into the transverse sinus over the anterior portion of the left atrium to serve as a vectored energy return path that enhances lesion formation connecting the right and left pulmonary vein ostial regions with a linear or other conduction block, also known as a left atrial "dome lesion".

Once the desired positioning of the one or more electrically conductive portions of a first and/or second medical devices has been achieved, the IEP ablation may proceed employing one or more of the energy delivery characteristics described above. For example, a string of biphasic pulses may be delivered over a brief period, with each train or train segment comprised of 40 pulses over 8 milliseconds at a frequency gated to one pulse train delivered at each onset of depolarization of the myocardium for a series of five heartbeats to effect ablation of the targeted cardiac tissue by IEP. Exemplary pulse trains may include a biphasic pulse width of 5 microseconds and inter-pulse interval of 20 microseconds, for example. Other waveforms can also be employed, having differing parameters such as shapes, amplitudes, pulse duration, interval between pulses, combination of pulses, etc. For example, biphasic energy pulses may be applied at very short durations (on the order of 1 nanosecond-50 microseconds, up to 100 microseconds, in some embodiments in the range of 20-200 microseconds) to effectively ablate fatty areas of heart tissue. Further, trains of short biphasic pulses having low amplitude can be effective in the permeabilization of cells while minimizing thermal damage. Such delivered pulse trains of energy may include a plurality of pulses each having a cycle time of not more than 5 milliseconds, but preferably not more than 50 microseconds; an output voltage between approximately 200-2000 volts, preferably between 500 and 1000 volts at a pulse width between approximately 0.005 microseconds-5 milliseconds, preferably between 0.005 microseconds and 50 microseconds; and/or a series of pulse trains, with each train having between approximately 1-500 monophasic or biphasic pulses, preferably 10-100 pulses. Delivery of energy pulse trains are preferably timed to correspond with the onset of depolarization of the myocardium. Alternately the pulse trains may be delivered to myocardium that is fully polarized, just before normal sinus rhythm. By employing pulsed, high voltage energy to effectuate IEP ablation of cardiac tissue cells, effective lesions can be rapidly created at rates much less than those typically encountered with conventional radiofrequency ablation. Further, the applied current can be specifically directed to create very specific lesion patterns without the generation of excessive heat.

In addition to the parameters of the delivered, pulsed energy, in some embodiments, the system 10 and related cardiac ablation methods may be adapted to correlate delivery of energy with the natural or paced depolarization-repolarization cycle of the cardiac muscle in a beating heart. For example, the electrically conductive portions 24 of the medical device 12 may be used to sensing electrical activity propagating along cardiac tissue; or, alternatively, a separate electrical sensing component (not shown) apart from the medical device 12 can be employed. Regardless, the control unit 14 may interpret the sensed electrical activity, and based upon this interpretation, dictate and/or adjust timing of the delivery of the pulsed electroporation-causing energy by the treatment energy source.

The sensed, naturally-occurring electrical activity can be provided in the series of waveforms observed on an intracardiac electrogram (EGM) or electrocardiogram (ECG). As a point of reference, a typical ECG tracing of a normal heartbeat (or cardiac cycle) consists of a P wave, a QRS wave complex, and a T wave. During normal atrial depolarization, the main electrical vector is directed from the SA node towards the AV node and spreads from the right atrium to the left atrium. This correlates with the P wave on the ECG. The QRS wave complex is a representation on the ECG that corresponds with the depolarization of the ventricles. Because the ventricles contain more muscle mass than the atria, the QRS wave complex is larger than the P wave. Finally, the T wave represents the repolarization (or recovery) of the ventricles. In other words, the QRS wave complex is an indication that the cardiac myocytes in the ventricles have depolarized, causing contraction of the heart. The T wave is an indication that the ventricular cardiac myocytes have repolarized and are prepared to repeat the depolarization observed again as a QRS wave complex.

Given the above, the system 10 may time the delivery of high voltage, pulsed energy as a function of the sensed cardiac cycle to which the delivery of pulsed, high voltage energy is guided. Further, the determined timing may be modified and/or selected not only based on the sensed/paced cardiac cycle, but also of the specific tissue to be ablated. For example, with ventricular cardiac tissue, high density energy pulses (as described above) may be applied during the QRS wave complex or segment. During the QRS wave complex, the ventricular cells are actively pumping ions through the cell membranes to effect depolarization. By timing the pulsed, electroporation energy with this period, the high voltage energy may be applied when the local cellular lethal threshold for high voltage pulses is reduced. This, in turn, allows more efficient use of the applied high voltage to cause cell death and local conduction block. Notably, with embodiments in which the delivery of pulsed, high voltage is tailored as a function of heart rate, frequencies of less than 1 Hz are beneficial.

The time or gated delivery of high voltage, pulsed energy can assume a different format where the tissue to be ablated is atrial tissue. More particularly, the pulsed, high voltage energy can be optimized in ablation of atrial myocardium using the P wave portion of the ECG recording as the gating reference point in the cardiac cycle. The atrial myocardium cells exhibit a reduced threshold for high voltage pulses when depolarizing; by timing the delivery or gating of pulsed, high voltage energy to correspond with the P wave segment, enhanced cardiac ablation or atrial tissue is promoted with lower output voltage gradients.

The tissue ablation systems and methods of the present disclosure provide a marked improvement over previous applications. The IEP energy delivery may be performed with a series of microsecond or nanosecond duration, high voltage pulses. The delivery is non-thermal and does not require saline irrigation to cool the electrodes. Accordingly, heat-sink issues encountered with conventional thermal ablations are eliminated, including the problem of irrigation fluid overload in fluid compromised patients during an atrial fibrillation ablation procedure. Further, the duration of IEP energy delivery may extend for a matter of seconds rather than minutes on end, which is a major reduction in time required to perform a procedure. In addition, IEP ablation eliminates the risk of complications such as esophageal fistulae, pulmonary vein stenosis, and phrenic nerve palsy associated with other ablation techniques and durations. Further, radiofrequency hyperthermal ablation may disrupt the cardiac endothelial surface, activate the extrinsic coagulation cascade, and lead to char and thrombus formation, which in turn may lead to systemic thromboembolism—all of which IEP avoids It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. An electrosurgical system, comprising:
 a treatment energy source being configured to:
  deliver at least one train of 10 to 60 biphasic electroporation pulses, each of the at least one train of 10 to 60 biphasic electroporation pulses lasting at most approximately 50 milliseconds, each of the 10 to 60 biphasic electroporation pulses of each of the at least one train of 10 to 60 biphasic electroporation pulses having a pulse width of between 3 µs and 5 µs, and delivery of the electroporation energy at an output voltage that is between 800 and 2000 volts.

2. The electrosurgical system of claim 1, wherein the output voltage is between 800 and 1000 volts at a current in a range of between 8 and 25 Amps.

3. The electrosurgical system of claim 1, wherein each of the at least one train of 10 to 60 biphasic electroporation pulses includes 40 biphasic electroporation pulses and lasts 8 milliseconds.

4. The electrosurgical system of claim 3, wherein each of the 40 biphasic electroporation pulses has a pulse width of 5 µs and an inter-pulse interval of 20 µs.

5. The electrosurgical system of claim 1, wherein the output voltage is between 800 and 1000 volts and each of the 10 to 60 biphasic electroporation pulses has a pulse width of 3 µs.

6. An electrosurgical system, comprising:
 a treatment energy source configured to deliver electroporation energy, the electroporation energy:
  including at least one train of 10-60 biphasic electroporation pulses, each of the at least one train of 10-60 biphasic electroporation pulses lasting at most approximately 50 milliseconds, each of the 10 to 60 biphasic electroporation pulses of each of the at least one train of 10 to 60 biphasic electroporation pulses having a pulse width between 3 µs and 5 µs; and
  including a cycle length of approximately 800 µs,
 the treatment energy source being further configured to deliver the electroporation energy at an output voltage that is between 800 and 2000 volts at a current in a range of between approximately 8 and approximately 25 Amps.

7. The electrosurgical system of claim 6, further comprising a medical device including a plurality of electrodes in electrical communication with the treatment energy source.

8. The electrosurgical system of claim 7, wherein each of the plurality of electrodes includes an electrically conductive surface and an electrically insulated surface.

9. The electrosurgical system of claim 6, wherein each of the 10 to 60 biphasic electroporation pulses has an inter-pulse interval of 20 µs.

* * * * *